US006812245B2

(12) United States Patent
Cañedo et al.

(10) Patent No.: US 6,812,245 B2
(45) Date of Patent: Nov. 2, 2004

(54) POLYCYLIC XANTHONES AND THEIR USE

(75) Inventors: Librada Maria Cañedo, Leon (ES); Dolores Garcia Gravalos, Madrid (ES); Francisco Romero, Leon (ES); Fernando Espliego, Leon (ES); Julia Perez-Baz, Leon (ES)

(73) Assignee: Instituto Biomar S.A. (ES)

( * ) Notice: Subject to any disclaimer, the term of this patent is extended or adjusted under 35 U.S.C. 154(b) by 0 days.

(21) Appl. No.: 10/312,343

(22) PCT Filed: Jun. 29, 2001

(86) PCT No.: PCT/GB01/02898

§ 371 (c)(1),
(2), (4) Date: Jun. 9, 2003

(87) PCT Pub. No.: WO02/00663

PCT Pub. Date: Jan. 3, 2002

(65) Prior Publication Data

US 2004/0009928 A1 Jan. 15, 2004

(30) Foreign Application Priority Data

Jun. 29, 2000 (GB) .............................................. 0016020

(51) Int. Cl.$^7$ ...................... A61K 31/35; C07D 493/02
(52) U.S. Cl. ..................... 514/453; 514/25; 549/275; 536/4.1
(58) Field of Search .................. 549/275; 536/4.1; 514/25, 453

(56) References Cited

U.S. PATENT DOCUMENTS

| 4,814,449 A | 3/1989 | Chang-qing et al. |
| 5,096,907 A | 3/1992 | Carter et al. |
| 5,223,430 A | 6/1993 | Carter et al. |

FOREIGN PATENT DOCUMENTS

| EP | 0 054 801 | 4/1985 |
| EP | 0 259 496 A | 3/1988 |
| EP | 0 353 381 A | 2/1990 |
| EP | 0 405 151 A | 1/1991 |
| EP | 0 442 003 A | 8/1991 |
| EP | 0 246 091 B1 | 10/1993 |
| EP | 1 292 299 B1 | 3/2003 |
| JP | 62 270 527 A | 11/1987 |
| JP | 62 270 587 A | 11/1987 |
| WO | WO 01/087283 | 11/2001 |

OTHER PUBLICATIONS

Bergeron et al., "Antineoplastic and Antiherpetic Activity of Spermidine Catecholamide Iron Chelators", *Biochemical and Biophysical Research Communications*, 121(3):848:854(1984).

Carter et al.,"Citreamicins, Novel Antibiotics from Micromonospora Citrea: Isolation, Characterization, and Structure Determination", *J. Antibiot.*, 43(5):504–512 (1990).

Guerrant et al., "Determination of Monosaccharides as Aldononitrile, O–Methyloxime, Alditol, and Cyclitol Acetate Derivatives by Gas Chromatography", *Analytical Chemistry*, 56:633–638 (1984).

Hasegawa et. al., "A Rapid Analysis for Chemical Grouping of Aerobic Actinomycetes", *J. Gen. Appl. Microbiol.*, 29:319.322 (1983).

Maiese et al.,"LL–El9085α, A Novel Antibiotic from Micromonospora Citrea: Taxonomy, Fermentation and Biological Activity", *J. Antibiot.*, 42(6):846–851 (1989).

Malkina et al., "167–A, A New Antibiotic Produced by a Mutant of an Inactive Wild Strain of Amycolata Autotrophica", *J. Antibiot.*, 47(3):342–348 (1994).

Nakagawa et al., "Enhanced Antimicrobial Activity of Acetyl Derivatives of Cervinomycin", *J. Antibiot.*, 39(11):1636–1639 (1986).

Nakagawa et al., "Structure of Cervinomycin, A Novel Xantone Antibiotic Active Against Anaerobe and Mycoplasma", *J. Antibiot.*, 40(3):301–308 (1986).

Omura et al., "Cervinomycin $A_1$ and $A_2$, New Antibiotics Active Against Anaerobes, Produced by Streptomyces Cervinus Sp. Nov.", *The Journal of Antibiotics*, 35(6):645.652 (1982).

Omura et al., "Structure of Cervinomycin, a Novel Antianaerobic Antibiotic", *J. Am. Chem. Soc.*, 108:6088–6089 (1986).

Shirling et al., "Methods for Characterization of Streptomyces Species". *Int. J. Syst. Bacteriol.*, 16(1):313–340 (1966).

Van der Auwera at al., "Indentification of Bacteriodes by Cellular Fatty Acid Profiles: Applicaton to the Routine Microbiological Laboratory", *J. Microbiol. Methods*, 4(5/6):267–275 (1986).

Waksman, "vol. II: Classification, Identification and Descriptions of Genera and Species", The Actinomycetes, p. 331 (1961).

*Primary Examiner*—Amelia A. Owens
(74) *Attorney, Agent, or Firm*—Fish & Richardson P.C.

(57) ABSTRACT

A novel class of antitumour compounds has been recognised based on the isolation from a new marine microbe, strain PO13-046, belonging to the genus *Actinomadura* sp.), of a compound designated IB-00208. The class of the formulae (I) or (II) where $R^1$ can be hydrogen, acyl, alkyl, alkenyl, aryl, benzyl, alkali metal, and/or sugar, and $R^2$ and $R^3$ can be hydrogen, alkyl, or together $R^2$ and $R^3$ form an unsaturated bond. Such compounds demonstrate an interesting activity several cancel cell lines and against Gram-positive bacteria.

4 Claims, 9 Drawing Sheets

POLYCYLIC XANTHONES AND THEIR USE

BACKGROUND OF THE INVENTION

Cervinomycins (EP00246091; EP0054801; J.Antibiot. 1982, 35, 645–652; J.Am.Chem.Soc. 1986, 108, 6088–6089, J.Antibiot. 1987, 40, 301–308; J.Antibiot. 1994, 47, 342–348; synthetic derivatives J.Antibiot. 1986, 39, 1636–1639 and EP0259496) and citreamicins (J.Antibiot. 1989, 42, 846–851; J.Antibiot. 1990, 43, 504–512; EP0405151) are members of a family of naturally occurring antibiotics, all of which posses a xanthone based unit embedded within a larger polycyclic framework.

These compounds have demonstrated potent activity against aerobic and anaerobic bacteria and mycoplasma, but only cervinomycins have been described to display antitumour activity (EP0246091).

R = Me, Cervinomycin A$_2$
R = H, 18-O-Demethyl cervinomycin A$_2$

We have recently described also the antitumour activity of citreamicins in PCT/GB01/02148.

| | R$^1$ | R$^2$ |
|---|---|---|
| Citreamicin α | COCH$_2$CH(CH$_3$)$_2$ | CH$_3$ |
| Citreamicin β | COCH(CH$_3$)$_2$ | CH$_3$ |
| Citreamicin γ | COCH$_3$ | CH$_3$ |
| Citreamicin ε | COCH$_2$CH(CH$_3$)$_2$ | H |
| Citreamicin η | H | CH$_3$ |

New anticancer drugs are still needed for treatment against many human tumours. Accordingly, a goal of the present invention is to provide new antitumour agents with a polycyclic xanthone structure.

Another objective of this invention is to provide pharmaceutical compositions for administering to a patient in need of treatment an active compound.

Yet another object is directed to the production of the polycyclic xanthone by controlled aerobic fermentation using a biologically pure culture of an organism in appropriate nutrient media, also to provide with methods for its recovery and concentration from the fermentation broth, and to the final purification of the active compound.

SUMMARY OF THE INVENTION

This invention provides a new class of active xanthone compounds founded on the discovery of a new compound IB-00208 isolated from a bacteria, useful as antitumour medicaments with the formula:

IB-00208

Thus, the present invention provides compounds with the general formula:

where each R$^1$ is the same or different and can be hydrogen, acyl, alkyl, alkenyl, aryl, benzyl, alkali metal, and/or sugar, and R$^2$ and R$^3$ can be hydrogen, alky, or together form an unsaturated bond.

This invention also provides processes for preparing such compounds including a process of obtaining IB-00208.

DETAILED DESCRIPTION OF THE INVENTION

IB-00208 and related compounds exhibits antitumour activity against mammalian tumours, such as human lung carcinoma, human colon carcinoma, human melanoma, etc. Thus, the invention includes a method of treating any mammal affected by a malignant tumour sensitive to them, which comprises administering to the affected individual a therapeutically effective amount of the compound or a pharmaceutical composition thereof.

The present invention also relates to pharmaceutical preparations which contain as active ingredient compound IB-00208 or any of its derivatives, or a pharmaceutical acceptable salt thereof, as well as the processes for its preparation. A pharmaceutically acceptable carrier is employed.

Pharmaceutical compositions are typically formulated from the active compound and include any solid (tablets, pills, capsules, granules, etc.) or liquid (solutions, suspensions or emulsions) in combination with any carrier or other pharmacologically active compounds.

The correct dosage of a pharmaceutical composition of IB-00208 or its derivatives will vary according to the particular compound, formulation, mode of application, and sites of host and tumour being treated.

Others factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The acyl groups can be aliphatic acyl, aromatic acyl, or mixed aliphatic/aromatic acyl. Thus, for example, they can be of the formula RCO—, where R is an alkyl group, an alkenyl group, an aryl group, an arylalkyl group, or an alkylaryl group. Examples include benzoyl.

The alkyl groups typically have from 1 to 18 carbon atoms. Alkyl groups preferably have from 1 to about 12 carbon atoms, more preferably 1 to about 8 carbon atoms, still more preferably 1 to about 6 carbon atoms, and most preferably 1, 2, 3 or 4 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members. The alkyl groups may be straight chain or branched chain.

The alkenyl groups typically have from 1 to 18 carbon atoms. Preferred alkenyl groups in the compounds of the present invention have one or more unsaturated linkages and from 2 to about 12 carbon atoms, more preferably 2 to about 8 carbon atoms, still more preferably 2 to about 6 carbon atoms, even more preferably 2, 3 or 4 carbon atoms. The term alkenyl as used herein refer to both cyclic and non-cyclic groups, although straight or branched noncyclic groups are generally more preferred.

The aryl groups can be carbocyclic or heterocyclic, and may have one or more fused rings. The carbocyclic aryl groups typically have 6 or 10 carbon atoms, as in phenyl or naphthyl. Heterocyclic aryl groups typically have 5 to 12 atoms, more usually 4, 5, 6, 10, 11 or 12 atoms, of which there is 1, 2, 3 or more heteroatoms usually chosen from oxygen, sulphur or nitrogen. Suitable heterocyclic aryl groups in the compounds of the present invention include coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzothiazol.

Notable alkali metals include sodium or potassium.

Sugars employed as substituents are typically mono-, di- or tri-saccharides or saccharide derivatives, prepferably mono- or di-saccharides. Pentose or hexose compounds are preferred. Derivatives include sugar glycosides, N-glycosylamines, O-acyl derivatives, O-methyl derivatives, sugar alcohols, sugar acids, deoxy sugars, and related compounds. Examples include the trimethyldeoxy-pyranose hexose of IB-00208.

This invention describes a new polycyclic xanthone IB-00208, isolated from the fermentation broth of a microorganism, preferably *Actinomadura* sp. PO13-046, a culture of which has been deposited in the Colección Española de Cultivos Tipo at the University of Valencia, Spain under the accession number CECT 5318. This deposit has been made under the provisions of the Budapest Treaty and all restrictions on the availability thereof to the public will be made upon the granting of a patent on this application.

The microbial strain was isolated from an unidentified marine polychaete collected at the Bay of Biscay.

While the deposited organism is clearly preferred, the present invention is not restricted or limited to any particular strain or organisms. It is the intention of the present invention to include other IB-00208 producing organisms, strains or mutants within the scope of this invention.

*Actinomadura* sp. PO13-046 cultured under controlled conditions in a suitable medium produces the antibiotic IB-00208. This strain is preferably grown in an aqueous nutrient medium, under aerobic and mesophilic conditions.

The antibiotic IB-00208 can be isolated from the mycelial cake by extraction with a suitable mixture of solvent such as $CHCl_3:CH_3OH:H_2O$. The activity is concentrated in the lower layer. The extracts from two repeated extractions can be combined and evaporated to dryness in vacuo.

Separation and purification of IB-00208 from the crude active extract can be performed by the use of the proper combination of conventional chromatographic techniques.

BRIEF DESCRIPTION OF THE DRAWINGS

FIGS. 4, 5, and 6 are COSY 45, HMQC and HMBC spectra of purified IB-00208 respectively;

Figure 9:
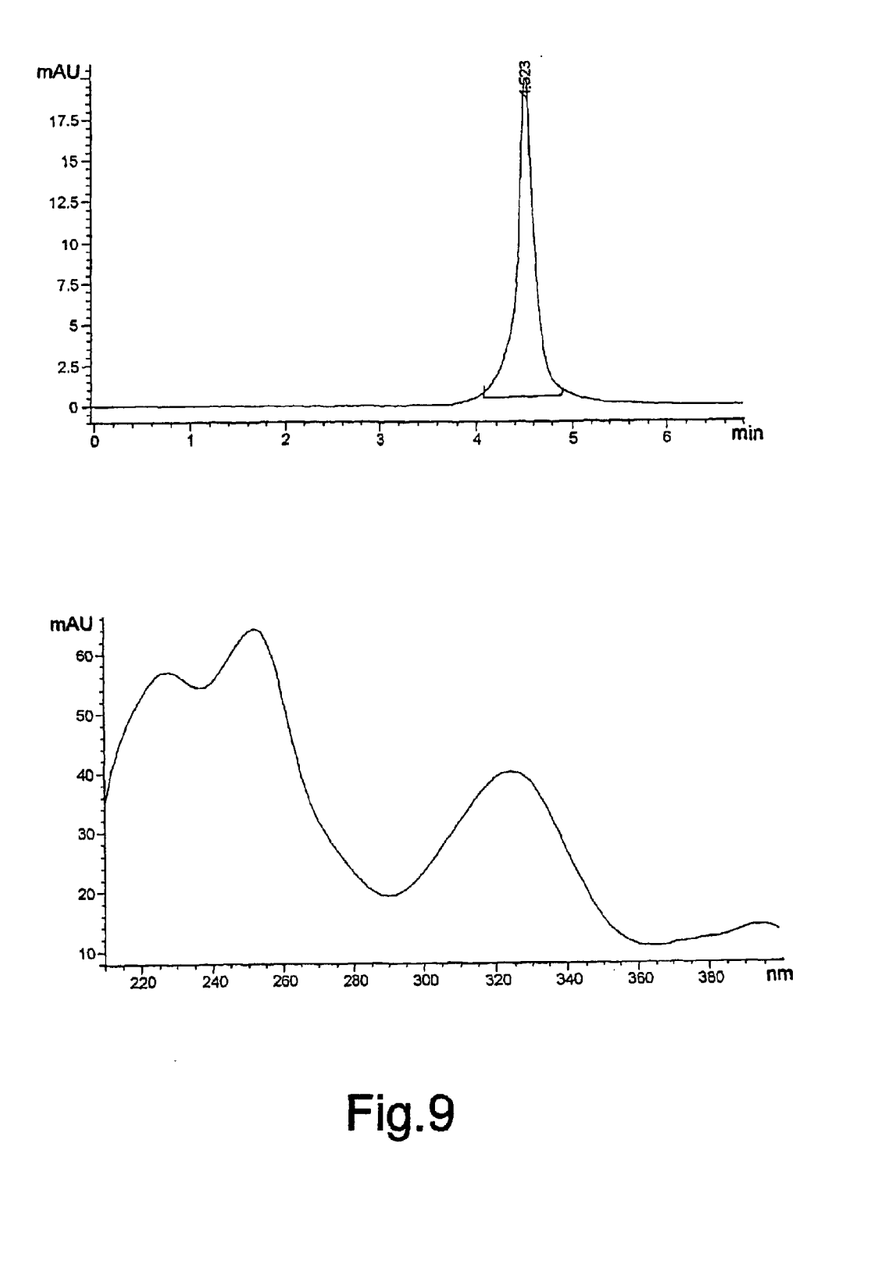
FIG. 9 is the HPLC/UV chromatogram and the UV spectrum of purified IB-00208

Fractionation can be guided by the antitumour activity of fractions, or by TLC visualised with vanillin in conc. $H_2SO_4$, or analytical HPLC with photodiode-array and MS detector. HPLC analysis is performed at room temperature using an analytical column Symmetry C18 (5 μm using as mobile phase methanol:$H_2O$:Acetic acid 99:1:1 and a flow rate of 0.3 ml/min. and plotted at 325 nm, in this conditions IB-00208 retention time is 4.5 min as is shown in FIG. 9.

On the basis of detailed analysis of their various spectral characteristics, the pure compound can be identified as IB-00208 (see data reproduced in FIGS. 1 to 9). Therefore the deduced structure is as it appears above.

IB-00208 data are summarised in Table 1.

TABLE 1

Figure 1:
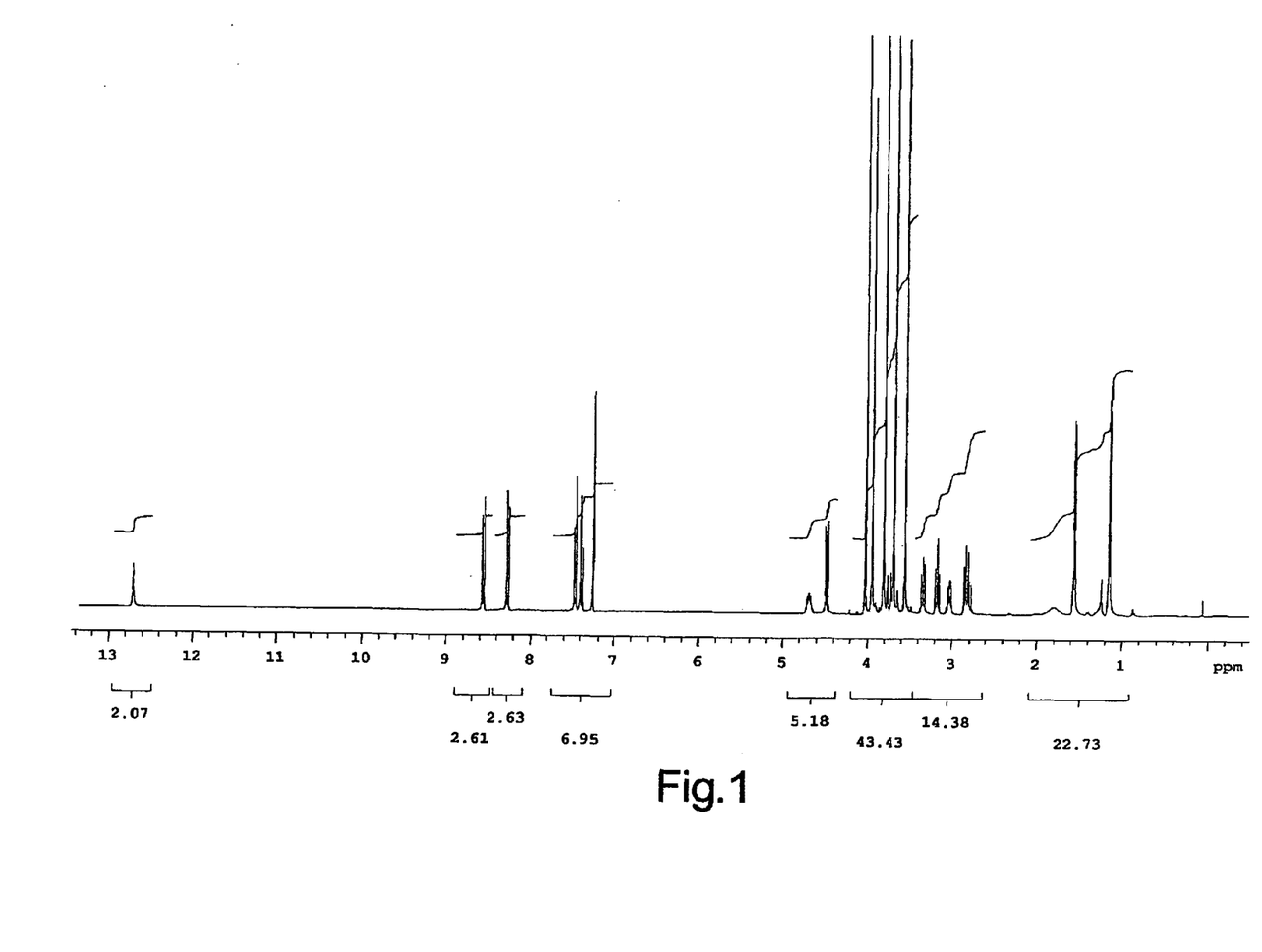
FIG. 1 is the proton NMR ($^1$H) spectrum of purified IB-00208.
Figure 2:
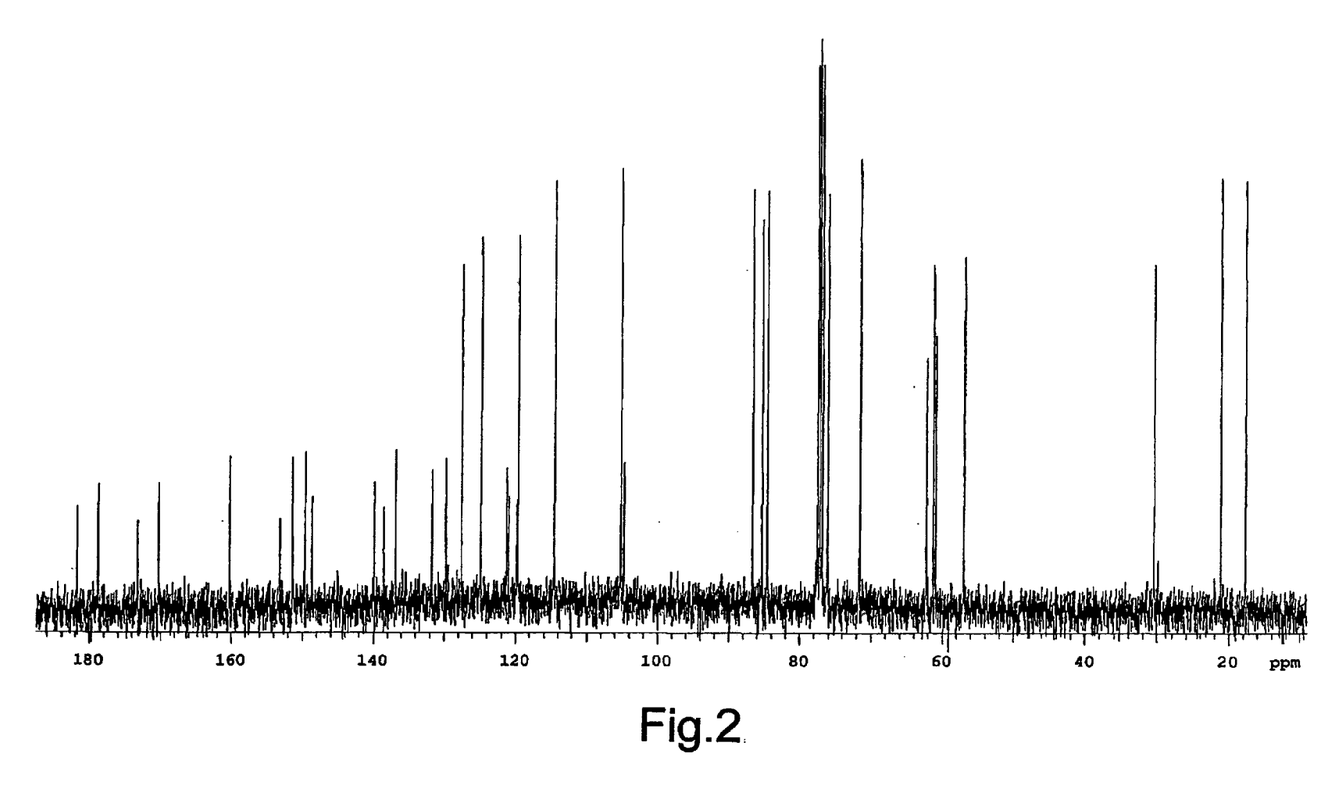
FIG. 2 is the carbon-13 NMR ($^{13}$C) spectrum of purified IB-00208.
Figure 3:
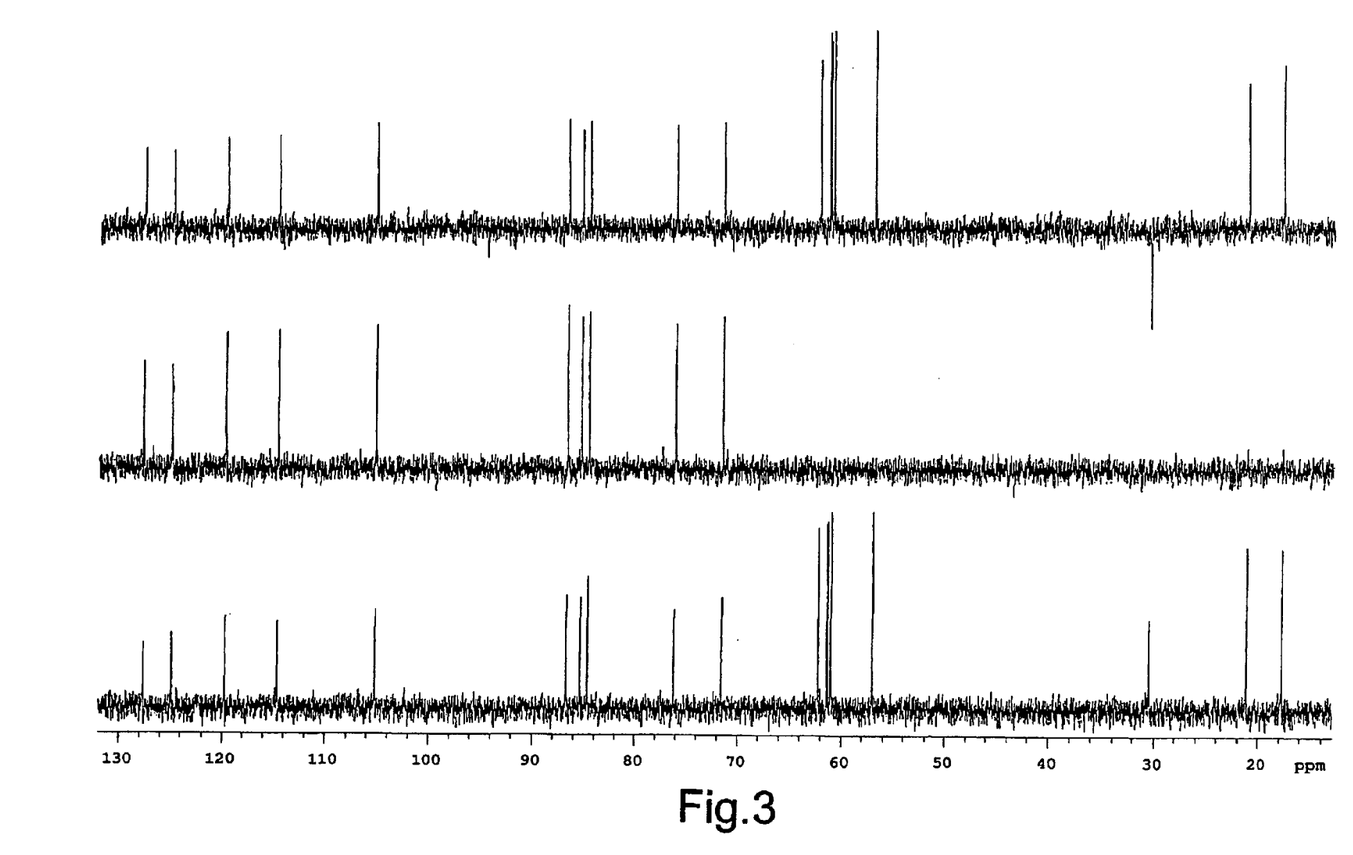
FIG. 3 is the DEPT experiment of purified IB-00208.
Figure 4:
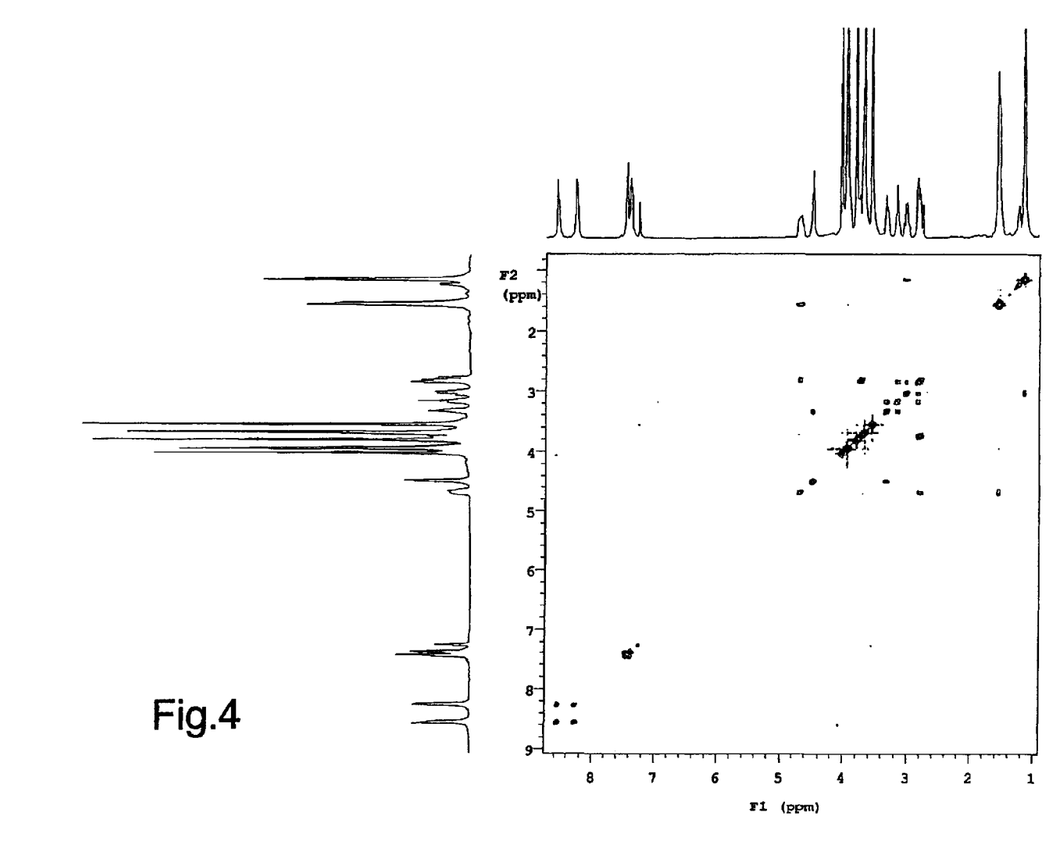
Figure 5:
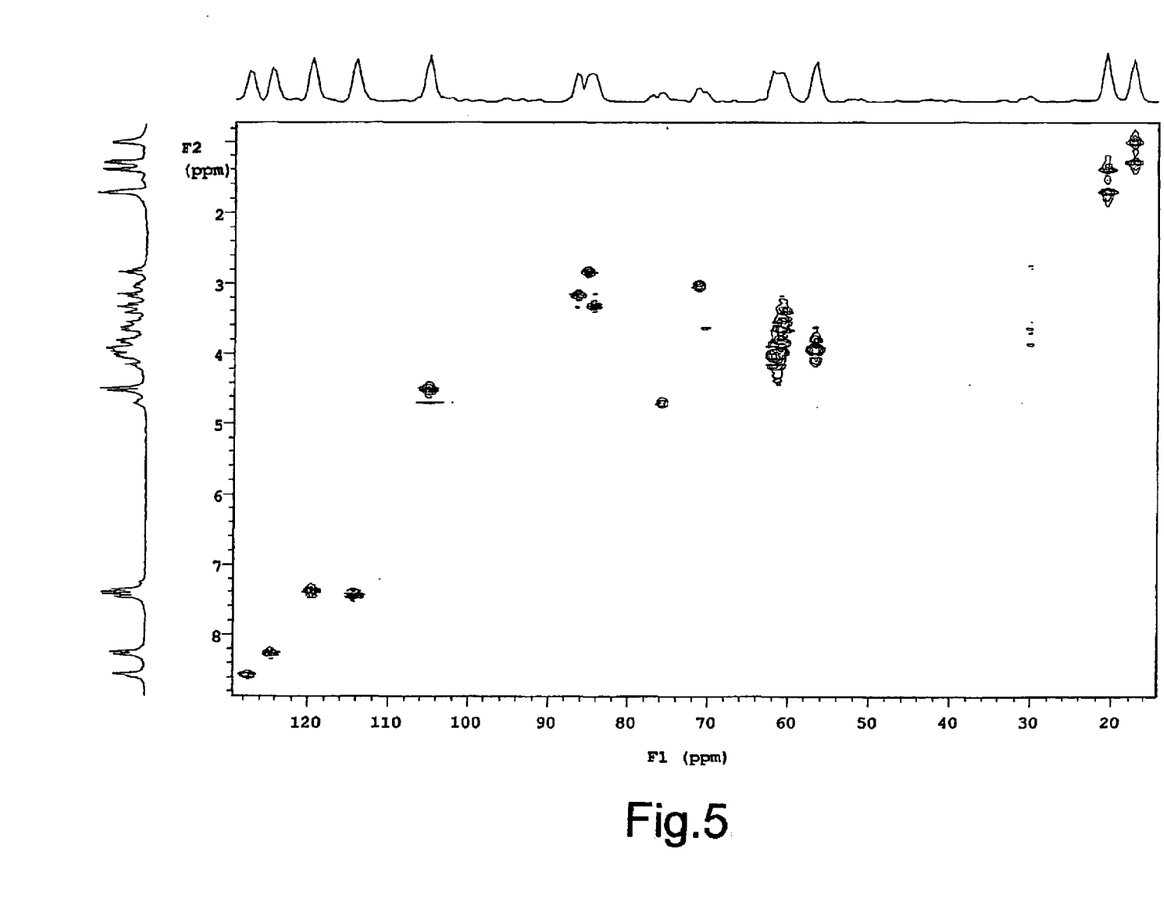
Figure 6:
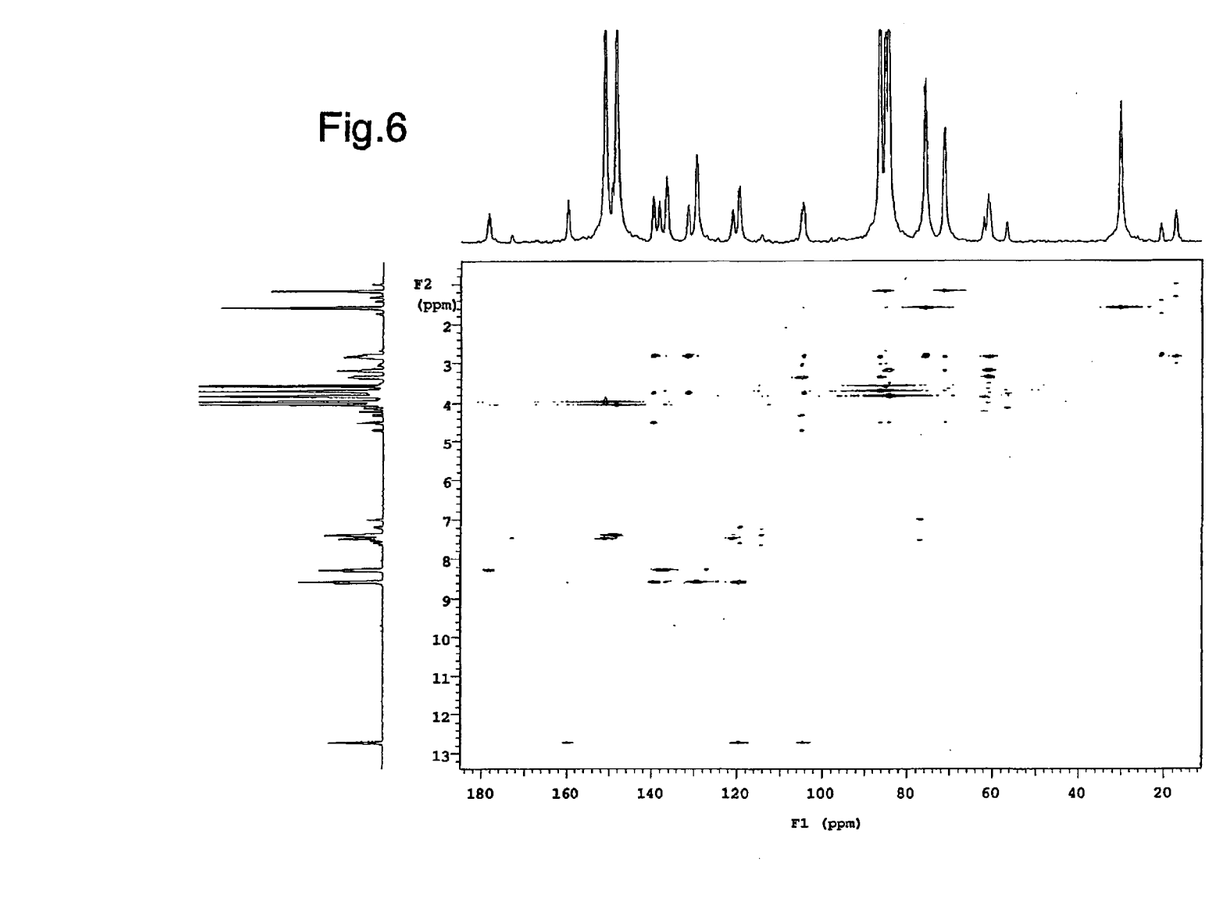
Figure 7:
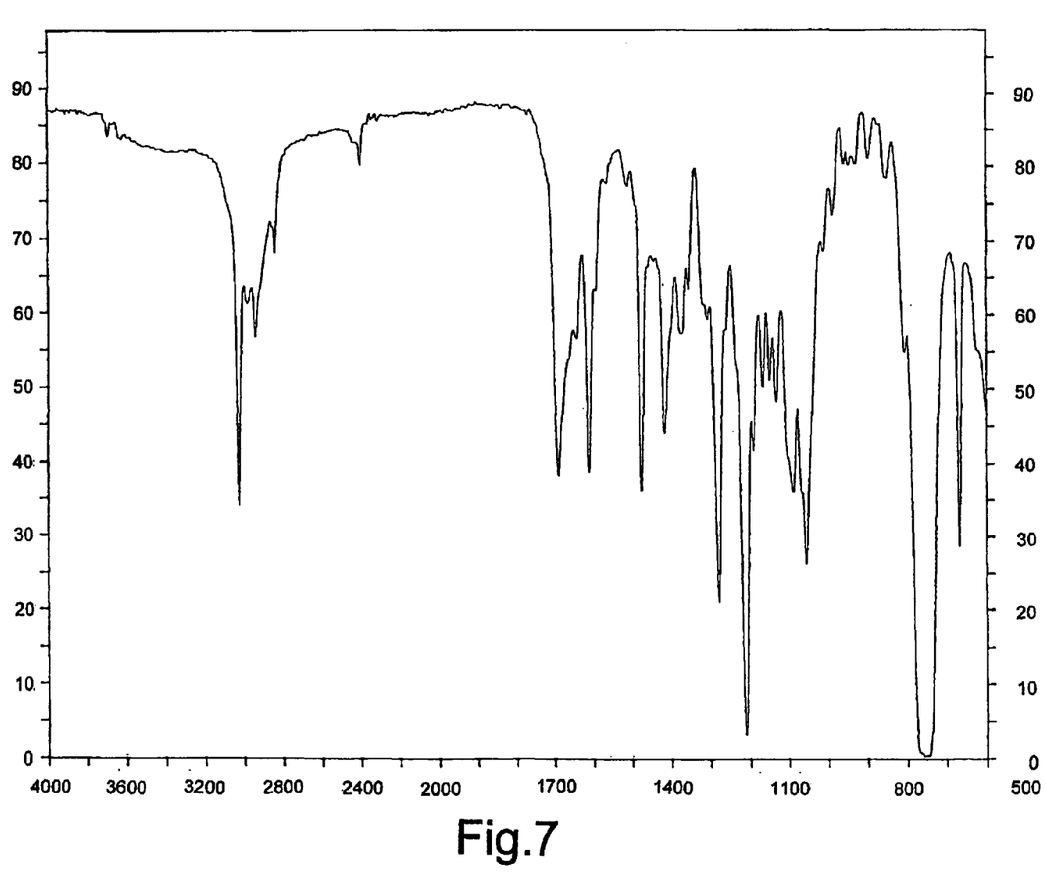
FIG. 7 is the IR spectrum of purified IB-00208.
Figure 8:
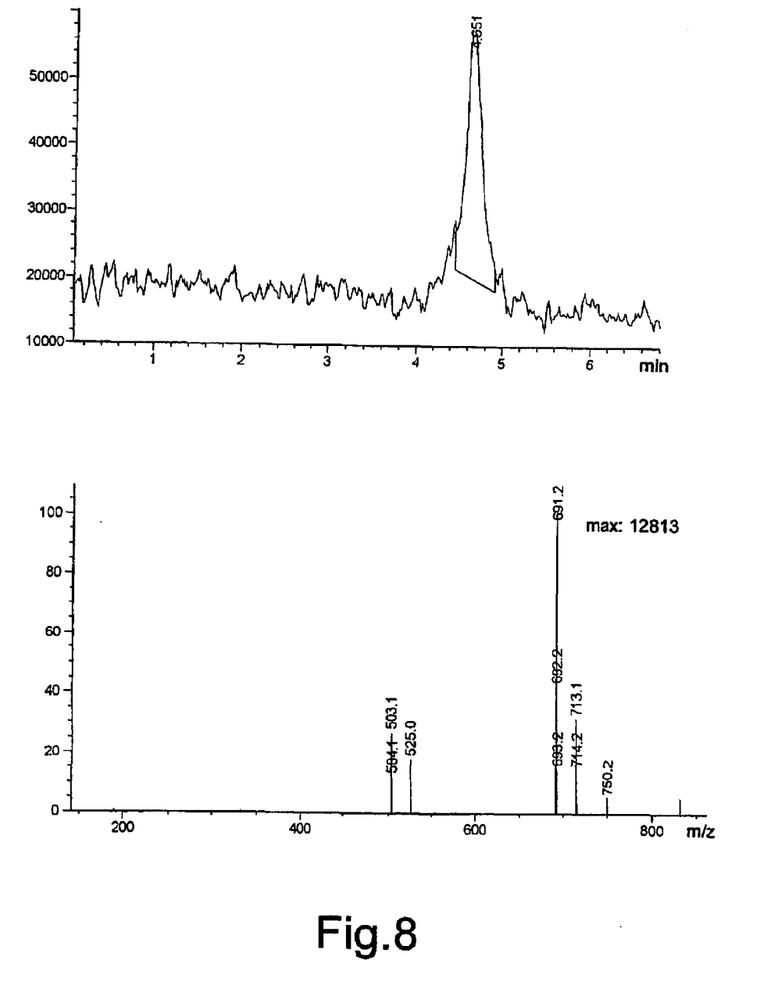
FIG. 8 is the HPLC/MS chromatogram and ESI-MS spectrum of IB-00208.

UV spectrum absorption maxima: 225, 255 nm and 325 nm as reported in FIG. 9.
$^1$H, $^{13}$C and DEPT NMR. spectra are reported in FIG. 1, FIG. 2 and FIG. 3 respectively.
2D NMR experiments COSY, HMQC and HMBC are reported in FIG. 4, FIG. 5 and FIG. 6 respectively.
Infrared absorption spectrum is shown in FIG. 7.
The ES-MS spectrum displayed a (M + H)⁻ peak at 691 and (M + Na) peak at 713, as reported in FIG. 8.

Various derivatives of IB-00208 can be prepared using techniques already known in the art. As an example, these modifications can be made using chemical or biological methods. These changes can include:

preparation of the aglycone moiety;

addition to the aglycone of different sugars known and new;

modification of the aglycone.

Compounds with a hydroquinone ring may be prepared from compounds with quinone ring by reduction of the quinone with a reducing agent [for example: NaBH4 (T. Ross Kelly et al. J.Am.Chem.Soc. 1989, 111, 4522–4524), Na2S2O4 (A. V. Rama Rao et al. Tetrahedron Lett. 1991,32, 5199–5202)] in an appropriate solvent, followed (when R1≠H) by reacting the hydroquinone with an acylating or alkylating or appropriated agent in an appropriate solvent.

The present invention in reference to preferred embodiments will be further illustrated with the following examples, which will aid in the understanding of the present invention and are aimed only to illustrate it, but which are not to be construed as limitations thereof.

EXAMPLES OF THE INVENTION

All percentages reported herein, unless specified, are presented by weight. All temperatures are expressed in degrees Celsius. All incubations are carried out at 28° otherwise stated and flasks are shaken in an orbital shaker at 250 rpm. All media and recipients are sterile and all culture processes aseptic.

Examples 1 to 3 deal with the preparation of compound IB-00208 with formula shown above, and Example 4 with its biological activity.

Example 1
The Producing Organism:

The taxonomic methods utilised herein are those usually employed in classic Actinomycete taxonomy and are reported in the literature.

All cultures after incubation were studied and records of results were made weekly up to 21 days. NaCl was added when needed.

A description of the organism is as follows:

After 21 days good growth was observed in ISP 2, ISP 6, Bennet and 172 ATCC with ASW. Colonies had light brown colour. In ISP 3, ISP 5, Czapek and ISP 7 with ASW less growth was obtained and no soluble pigment was observed. No aerial mycelium was formed. Substrate mycelium was branched. Isolated spores-over the substrate mycelium may occur. Spores are elongated and scarce. No other formations were observed.

In ISP-1 brown diffusible pigments were formed, as well as in other solid media. Resistance to NaCl was over 5%. The optimum growth temperature range is between 25° and 35° C. The organism can grow on glucose, galactose, rhamnose, and xylose as the sole carbon source, however, growth on fructose, raffinose, m-inositol, sucrose, and α-melibiose is negative, and in mannitol and melezitose is doubtful.

Chemical composition studies of the organism show that meso-2,6-diaminopimelic acid is present in the whole cell hydrolysate of strain PO13-046.

Fatty acids methyl esters comparison of PO13-046 with other similar strains is described in TABLE 2.

TABLE 2

|  | i-14:0 | 14:0 | 15:0 |
|---|---|---|---|
| PO13-046 | 1.75 | 2.43 | 4.9 |
| Actinomadura livida ATCC 33578 | 1.41 | 1.21 | 7.4 |
| Actinomadura madurae NRRL-B 5390 | 1.0 | 2.5 | 6.1 |
| Actinomadura malachitica ATCC 27888 | 1.4 | 3.4 | 0.7 |
| Actinomadura vinacea ATCC 33581 | 1.4 | 1.4 | 6.1 |
| Actinomadura formosensis[1] ATCC 49059 | 1.3 | 1.2 | 2.8 |
| Streptomyces griseus* DSM 40236 | 15.1 | 0.8 | 0.9 |

|  | i-16:0 | 16:1 | 16:0 |
|---|---|---|---|
| PO13-046 | 20.2 | 5.16 | 22.6 |
| Actinomadura livida ATCC 33578 | 21.8 | 5.5 | 13.7 |
| Actinomadura madurae NRRL-B 5390 | 11.5 | 5.56 | 21.2 |
| Actinomadura malachitica ATCC 27888 | 18.5 | 7.9 | 26.2 |
| Actinomadura vinacea ATCC 33581 | 22.7 | 6.8 | 15.2 |
| Actinomadura formosensis[1] ATCC 49059 | 22.5 | 3.4 | 17.8 |
| Streptomyces griseus* DSM 40236 | 21.2 | 5.1 | 6.4 |

|  | 17:1 | 17:0 |
|---|---|---|
| PO13-046 | 6.5 | 5.4 |
| Actinomadura livida ATCC 33578 | 14.9 | 7.0 |
| Actinomadura madurae NRRL-B 5390 | 10.9 | 7.9 |
| Act. malachitica ATCC 27888 | 1.1 | 0.9 |
| Actinomadura vinacea ATCC 33581 | 12.8 | 5.6 |
| Actinomadura formosensis[1] ATCC 49059 | 6.9 | 4.6 |
| Streptomyces griseus* DSM 40236 | <1 | <1 |

|  | i-18:1 | i-18:0 | Cis-18:1 | 18:0 | 18.38 |
|---|---|---|---|---|---|
| PO13-046 | 5.2 | 1.8 | 13.0 | 1.22 | 5.75 |
| Actinomadura livida ATCC 33578 | 7.5 | 1.2 | 7.8 | 1.0 | 5.7 |
| Actinomadura madurae NRRL-B 5390 | 3.0 | 1.6 | 16.5 | 1.1 | 5.3 |
| Act. malachitica ATCC 27888 | 3.7 | 2.7 | 15.8 | 4.5 | 8.7 |
| Actinomadura vinacea ATCC 33581 | 6.1 | 1.6 | 10.3 | 0.7 | 5.1 |
| Actinomadura formosensis[1] ATCC 49059 | 6.8 | 1.8 | 10.8 | 2.4 | 5.5 |
| Streptomyces griseus* DSM 40236 | 1.1 | <1 | <1 | <1 | <1 |

*i-15:0 (9.2%), a-15:0 (19.6%), i-17:0 (1.7%), and a-17:0 (3.25%) are important fatty acids for Streptomyces but are minor constituent in Actinomadura.
[1]Actinomadura formosensis formerly Thermonospora formosensis.

Based on the preceding characteristics the culture is determined as a species of the genus Actinomadura, with 94% similarity to A. vinacea type strain.

Example 2
Fermentation of IB-00208:

The required steps needed for the production of IB-00208 by the preferred organism are:

Stock Culture: Whole broth of a pure culture of Actinomadura sp. strain PO13-046 is preserved frozen in 20% glycerol.

Inoculum: A frozen culture or a well grown slant culture is used to seed 100 ml of seed medium described previously in a 250 cc shake flask. The flask is incubated during 48 hrs, and used as a first stage inoculum. 500 ml of the same medium in 2 L Erlenmeyer flask are seeded with 10% of this first stage inoculum. The flask is incubated during 48 h.

Fermentation: With 2.5 L of second stage inoculum seed 50 L of production medium already described in a 75 L fermentation tank. The fermentation is carried out during 96 hours with 400 rpm agitation and air flow of 0.5 V/V.M.

TABLE 3

| Inoculum medium: | |
| --- | --- |
| Glucose | 5 g |
| Starch | 20 g |
| Beef extract | 3 g |
| Yeast extract | 5 g |
| Tryptone | 5 g |
| CaCO3 | 4 g |
| NaCl | 5 g |
| KCl | 0.5 g |
| MgCl2 | 2 g |
| Tap water | to 1,000 ml |
| Production medium: | |
| Glucose | 5 g |
| Starch | 20 g |
| Soybean meal | 15 g |
| Yeast extract | 5 g |
| Tryptone | 2 g |
| CaCO3 | 4 g |
| NaCl | 5 g |
| KCl | 0.5 g |
| MgCl$_2$ | 2 g |
| Tap water | to 1,000 ml |

Yield of IB-00208 can be monitored by whole broth assay against murine leukaemia P-388 or by HPLC.

Example 3

Isolation of IB-00208:

4.5 liters of whole harvested broth were filtrated to separate the biomass and other solids. The mycelia cake was extracted twice with a mixture solvent (1.5 l) of CHCl$_3$:CH$_3$OH:H$_2$O (2:1:1), the activity was concentrated in the lower layer. The organic solvent was concentrated and evaporated to dryness in vacuo to yield 1.2 g of crude extract.

The extract was chromatographed on silica gel using a mixture of n-hexane/ethyl acetate and ethyl acetate/methanol as eluting solvents. 110 mg of a fraction containing IB-00208 with antitumour activity were eluted with ethyl acetate/methanol 1:1.

Further purification of the fraction containing IB-00208 was achieved by column chromatography on silica gel and 18 mg of pure compound IB-00208 were eluted with chloroform/methanol 95:5.

Example 4

Biological Activity:

The antitumour activities of IB-00208 have been determined in vitro in cell cultures of mouse leukaemia P-388, human lung carcinoma A-549, human colon carcinoma HT-29 and human melanoma MEL-28. The procedure was carried out using the methodology described by Bergeron et al. The IC50 found was of 0.001, 0.001, 0.001, and 0.001 µg/ml for all 4 cell lines.

References

The following references have been cited herein:

ATCC Catalog 1996.

Bergeron et al. Biochem.Biophys.Res.Comm. 121:848, 1984

Guerrant and Moss, Anal.Chem. 56:633, 1984.

Hasegawa et al., J. Gen. Appl. Microbiol. 29:319, 1983.

Shirling and Gotlieb. Int.J.Syst.Bacteriol. 16:313, 1966.

Van der Auwera et al., J. Microbiol. Methods, 4:265, 1986.

Waksman, The Actinomycetes vol.II:331, 1961.

The present invention has been described in detail, including the preferred embodiments thereof. However, it will be appreciated that those skilled in the art, upon consideration of the present disclosure, may make modifications and/or improvements within this invention.

What is claimed is:

1. A compound of the general formula:

where each $R^1$ is the same or different and can be hydrogen, acyl, alkyl, alkenyl, aryl, benzyl, alkali metal, and/or sugar, and $R^2$ and $R^3$ can be hydrogen, alkyl, or together $R^2$ and $R^3$ form an unsaturated bond.

2. A compound according to claim 1 of formula:

3. An anti-tumour pharmaceutical composition comprising a compound according to claim 1 and a pharmaceutically acceptable carrier.

4. An anti-tumour pharmaceutical composition comprising the compound IB-00208 according to claim 2, and a pharmaceutically acceptable carrier.

* * * * *

UNITED STATES PATENT AND TRADEMARK OFFICE
CERTIFICATE OF CORRECTION

PATENT NO. : 6,812,245 B2  
DATED : November 2, 2004  
INVENTOR(S) : Librada Maria Canedo et al.

It is certified that error appears in the above-identified patent and that said Letters Patent is hereby corrected as shown below:

Title page,  
Item [56], References Cited, U.S. PATENT DOCUMENTS,  
"4,814,449", replace "Chang-qing et al." with -- C.-Q Qi et al. --.

Column 1,  
Line 1, replace "POLYCYLIC" with -- POLYCYCLIC --.  
Line 2, insert -- The present invention relates to polycyclic xanthones and their use against tumours. --.

Signed and Sealed this

Eighteenth Day of October, 2005

JON W. DUDAS  
*Director of the United States Patent and Trademark Office*